(12) United States Patent
Fournier (10) Patent No.: US 7,298,499 B2
(45) Date of Patent: Nov. 20, 2007

(54) METHOD AND SYSTEM FOR CHARACTERIZING STRUCTURAL DAMAGE FROM OBSERVING SURFACE DISTORTIONS

(75) Inventor: Nicolas Fournier, Toulouse (FR)

(73) Assignee: Airbus France, Toulouse (FR)

( * ) Notice: Subject to any disclaimer, the term of this patent is extended or adjusted under 35 U.S.C. 154(b) by 123 days.

(21) Appl. No.: 11/088,787

(22) Filed: Mar. 25, 2005

(65) Prior Publication Data

US 2005/0246108 A1 Nov. 3, 2005

(30) Foreign Application Priority Data

Mar. 25, 2004 (FR) .................................. 04 03096

(51) Int. Cl.
*G01B 11/24* (2006.01)
(52) U.S. Cl. .................................... 356/605; 356/237.1
(58) Field of Classification Search ................ 356/605, 356/601, 603, 610, 618, 237.1, 237.2
See application file for complete search history.

(56) References Cited

U.S. PATENT DOCUMENTS

| 5,025,285 | A | 6/1991 | Schwarz |
| 5,311,286 | A | 5/1994 | Pike |
| 6,731,391 | B1 * | 5/2004 | Kao et al. .................... 356/605 |
| 6,809,803 | B1 * | 10/2004 | O'Brien et al. ............. 356/35.5 |

FOREIGN PATENT DOCUMENTS

EP 0 674 151 A2 9/1995

WO WO 00/39523 7/2000

OTHER PUBLICATIONS

Juan Antonio Quiroga, et al., "Isotropic n-dimensional fringe pattern normalization", Optics Communications vol. 224, Sep. 2003, pp. 221-227.
Manuel Servin, et al., "Isochromatics demodulation from a single image using the regularized phase tracking technique", Journal of Modern Optics, vol. 48, No. 3, 2001, pp. 521-531.
Bernhard Ströbel, et al., "Processing of interferometric phase maps as complexed-valued phasor images", Applied Optics, vol. 35, No. 13, May 1, 1996, pp. 2192-2198.
Manuel Servin, et al., "Regularized Quadrature and Phase Tracking (RQPT) From a Single Closed-Fringe Interferogram", (CC/CIMAT), No. I-03-13, May 8, 2003, pp. 1-23.

(Continued)

*Primary Examiner*—Roy M. Punnoose
(74) *Attorney, Agent, or Firm*—Oblon, Spivak, McClelland, Maier & Neustadt, P.C.

(57) ABSTRACT

This process includes arranging a grid on the surface a structure to be inspected, directing a light source onto this grid so as to create a shadow on the structure, recording an image of the pattern observed, displaying a graphic representation of the image recorded, and determining a depth of the damage from this representation. The device enabling the implementation of the process includes a grid or screen, a light sources, an image acquisition device, and a display. Once the images are recorded, the invention calls upon processing devices that permit determining the position in space, in particular, a height, of each point of the image and as such of the surface observed.

17 Claims, 4 Drawing Sheets

OTHER PUBLICATIONS

J. C. Martinez-Anton, et al., "Enhancement of surface inspection by Moire interferometry using flexible reference gratings", Optics Express, vol. 8, No. 12, Jun. 4, 2001, pp. 649-654.

J. C. Martinez-Anton, et al., "Shadow moiéand the use of flexible gratings to adapt to curved surfaces", Roma 2000, 4 pages.

* cited by examiner

METHOD AND SYSTEM FOR CHARACTERIZING STRUCTURAL DAMAGE FROM OBSERVING SURFACE DISTORTIONS

CROSS-REFERENCE TO RELATED APPLICATIONS

This application claims priority to French Application No. 04 03096, filed Mar. 25, 2004, the entire content of which is hereby incorporated by reference.

BACKGROUND OF THE INVENTION

1. Field of the Invention

This invention involves a structural non-destructive control system and in particular, a system for characterizing structural damage from observing surface distortions of said structure.

2. Discussion of the Background

Assessment of the structural damage, in other words, any structural problem that may affect its integrity, can be critical when used in severe environments. In the field of aeronautics for instance, impacts of miscellaneous objects on the structure of an aircraft can diminish mechanical features, especially, in the case of an impact at a sensitive location. Likewise, in the case of a distortion that took place during the manufacturing or assembly stages of a part, referencing of such defects is necessary.

When distortions are considerable, their characterization can be done directly by an inspection operator who is making a decision about what is to be done with the damage. Such decision generally involves making a choice between validation, repair or, in the most unfavorable cases, replacing the defective part.

When it involves small distortions, viewing with the naked eye shows its limits and generally requires that the inspection operator is very well trained. Thrusting aside these limits is even more important in the case of small surface distortions when the internal degradation of the structure is considerable.

Traditionally, to correct this problem, surfaces are tested using mechanical sensors that enable measuring a distortion with respect to a theoretical profile. However, these mechanical means are very difficult to implement whenever one attempts to inspect pieces in operation. Indeed, these devices are often not very practical and fragile and as such, are incompatible with unprotected environments. In addition to this, one must consider the risk of damage during the transportation of these inspection devices, not taking into account that the sensors generally used require an extensive implementation and have a high usage cost.

Moreover, for quality reasons, one may want to arrive at more precise results than those obtained with classical sensors. Indeed, for a defect with a small diameter but of considerable depth, the inspector may incorrectly assess the damage while the structural fatigue risks are very much present and may be important according to the position of the defect on the structure.

To improve the observation of the distortions, the use of optical principles has also been known.

In document EP 0 674 151, a viewing of the surface defects is done by means of a shadow moiré on the observed surface. It permits to point out the existence of a distortion of the surface by observing through a rigid grid or screen the shadow of the network of this grid or screen on the surface, projected by a light source. Such a device equipped with a rigid grid or screen is only used overhead with respect to the surface and in addition, does not give any quantitative information about the extent of the distortion.

Document WO 00/39523 tries to provide a response to this last problem. This document shows an overhead moiré grid or screen with respect to a structural surface to be observed and proposes to measure the extent of the distortion of the generated pattern through the projection of the grid image on the surface. This solution then requires comparison of the scope of the distortion with the results of the measurements made on samples for which the deformity is known. To obtain comparable results with those obtained on calibrated samples, adjustment of the grid incline is essential.

A problem of these devices resides in the fact that the grid is overhead. In practice, placing such devices overhead is difficult and going across the surface with them becomes practically impossible in particular when an accurate measuring instrument, like a micrometer, is used to incline the grid or screen a certain angle for each measurement.

Another problem encountered with the process indicated by document WO 00/39523 resides in the fact that all types of distortions must be known because afterwards they are compared with calibrated samples to permit characterizing the observed surface problems. Within the framework of assessing cold compression of a metal such as the one presented in the document in question, the device seems appropriate but as soon as one goes beyond a specific application and one looks to assess any type of surface distortion, the device is not very useful.

SUMMARY OF THE INVENTION

The purpose of this invention is to provide an easy to implement process and a device that permits characterizing a structural damage. Preferably, the device according to the invention will have a low cost price and will be easy to be transported.

For such purpose, this invention proposes a characterization process for a structural damage that includes the stages for bringing close to the surface of such a structure the moiré grid or screen, of directing the light source towards such grid or screen so as to create a shadow of said grid or screen on said structure, characterized by the fact that it also includes the following stages:

with a acquisition device, record an image of the pattern observed through the grid or screen according to an observation direction that differs from that of the light source;
  graphically represent the damage from such recorded image using a processing algorithm of said image;
  characterize the damage on the basis of such representation.

With such a process, said grid can beneficially be positioned directly on the surface to be analyzed to avoid long and demanding adjustments.

In a particular mode of the invention, the process can also include stages for running across the surface, of visually inspecting, whether or not through said acquisition devices, the existence or non-existence of distortions of said pattern, to stop the running across the surface, for instance, when a distortion shows up, to record an image thanks to the acquisition device and to characterize the damage.

In a special mode of implementation, the user can transfer one or several recorded and unprocessed images towards off-centered processing devices to characterize the damages later.

When processing the image of the observed pattern, the processing algorithm includes for instance a normalization stage of the interference fringes appearing on said image. This stage also permits eliminating the background of the pattern that would not be useful for characterizing a damage and for normalizing the observed phase field.

In another form of implementation, when processing said image, the algorithm permits for instance obtaining the phase modulation to determine the position in space of each point of said image, on the basis of the features of mounting and irradiance observed.

Beneficially, the result of the implementation stage of a graphic representation is a graphic representation according to a color scale. This scale can be beneficially representative of the depth of the damage, with the deepest damage points being represented for instance by a dark color while the rest of the damage may be colored differently from the zero height of the surface where the color would be lighter. The graphic representation can be a two-dimensional or a multiple dimensional view of the damage.

The invention also involves a device for the implementation of the process that includes:
  a support, preferably an opaque box to avoid interference light;
  a moiré grid or screen;
  a lighting device;
  a image acquisition device for which the observation axis is offset with respect to that of the lighting device;
  an image processing device;
  a display device for the result of said processing.

Beneficially, the moiré grid or screen shall be flexible to augment the contact surface between said grid or screen and the structure observed, in particular, when the latter is not flat.

According to a mode of implementation of the invention, said grid or screen undergoes an anti-reflection treatment, preferably prior to being used.

Beneficially, the image acquisition device is secured to the support to permit permanent observation from one and the same observation axis, thus assuring the user who is implementing the process of the invariability of the mounting features irrespective of the observation axis of the user himself.

The image acquisition device includes for instance a digital acquisition device permitting a photo or video recording.

Beneficially, said record is processed with processing devices such as a programmed computer, applying at least an image processing algorithm. These algorithms are for instances algorithms used in the process described above.

The result provided by the image processing devices, determining the positions of the damage points in space, is for instance then graphically transformed, globally represented or not represented on a screen, of a computer for instance, in color or in black and white by two or three-dimensional views. For this purpose, the device according to the invention includes advantageously devices for graphically transforming the result provided by the image processing device, a screen for viewing the graphic representation obtained, permitting a representation according to a color scale, by two or three dimensional views.

BRIEF DESCRIPTION OF THE DRAWINGS

Details and advantages of this invention will be brought out more by the description below, referenced against the attached schematic drawings on which.

DESCRIPTION OF THE PREFERRED EMBODIMENTS

Figure 1:
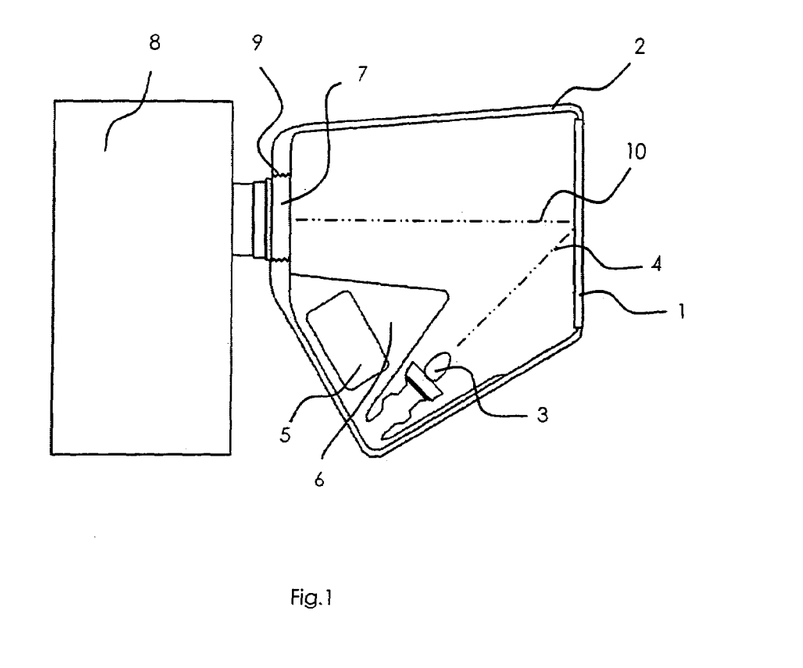
FIG. 1 is a schematic cross-section of a device according to the invention.

With regard to FIG. 1, this FIG. shows an overhead schematic view a device comprising in the first instance a moir grid or screen 1 secured to a support 2 as well as an image acquisition device 8 equipped with a lens.

In the implementation form shown, support 2 is a box, preferably opaque, to prevent light pollution. Moiré grid or screen 1 slides along the walls of the box up to a maximum position so that it no longer moves once positioned onto support 2. As a variant, the moiré grid or screen can be screwed onto support 2.

FIG. 1 also shows a light source 3, a diode for instance, that lights moir grid or screen 1 by emitting light along a lighting axis 4. This axis 4 makes an angle of, for example, between 40° and 50° —preferably 45° —on the plan of moir grid or screen 1.

As an implementation variant, support 2 can have a location 6 that permits making the device autonomous; this location 6 can for instance include an electrical battery 5. This location 6 is then preferably delimited by a separator that prevents the light coming directly from the diode from reaching the lens of the image acquisition device and as such, not to affect the irradiance measurements during the phase calculations explained below.

Image acquisition device 8 is secured onto an opening 7 for which support 2 is provided. This device is schematically shown here. For instance, it is a digital photo camera. For the implementation shown on the drawing, this digital photo camera is mounted by means of screw thread 9 (but it is understood that any other means of securing could be used here). Opening 7 and screw thread 9 enable the digital photo camera to photograph moiré grid or screen 1 according to an observation axis 10.

For the implementation example shown on the drawings, the mounting features, in other words, the observation 10 and lighting axes 4 are easily reproduced, without any risk of obtaining different information for one and the same damage as a result of a change thereof. Preferably, the angle between these two axes 4 and 10 is 45°.

Figure 2:
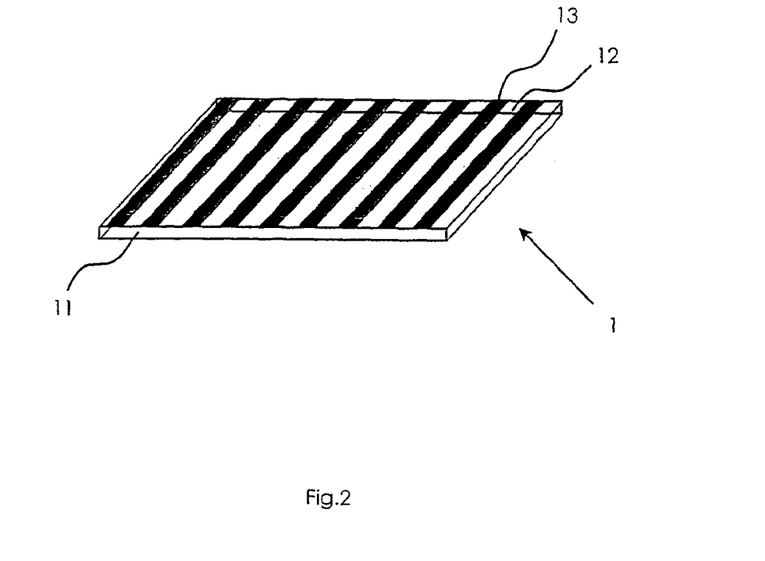
FIG. 2 shows a perspective of a moiré grid or screen.

About moiré grid or screen 1, when referring now to FIG. 2, one will be able to appreciate the technical features. This moiré grid or screen includes first of all a transparent support 11. Then, this grid presents a pitch defined by alternating on the top face of this transparent support 11 transparent strips 12 and dark strips 13. Dark strips 13 can for instance be silk screened on the top surface of transparent support 11. Necessarily, the thickness of this support is not zero. This observation permits to understand that by maintaining the plan of the grid above the sustaining plane of support on the surface to be analyzed, this feature permits observing fringes without lifting the device overhead, even when no damage is present. Still concerning the grid, one can also process the top surface of the grid to minimize reflections. Contrast of the pattern observed is then augmented.

To permit observation of the moiré fringes, grid or screen 1 is turned in such a way that its longitudinal bands 12, 13 do not form a zero angle with the alignment between image acquisition device 8 and light source 3, in other words, the plane containing lighting 4 and observation 10 axes. Preferably, longitudinal bands 12 and 13 will be perpendicular to this plane to observe the fringes in a more contrasted way.

Figure 3:
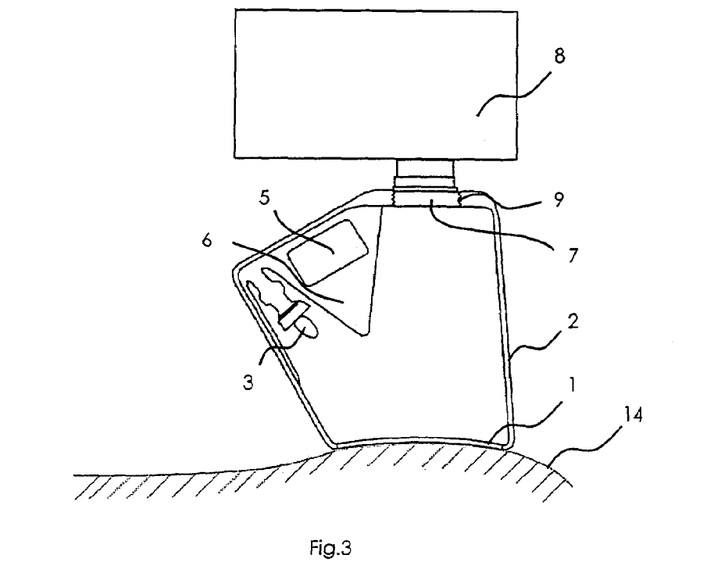
FIG. 3 illustrates the implementation of a process according to the invention on a surface that is not flat.

On FIG. 3, one sees how to apply moiré grid or screen 1 of the device on a surface 14 to be inspected that is not necessarily flat.

Before running across the surface, the image acquisition device parameters must be adjusted properly to obtain optimal results. Contrary to what one might believe, a good adjustment of the image acquisition device does not necessarily correspond to a maximum adjustment of the resolution. For instance, for a millimeter fault, a lesser resolution will suffice to characterize the damage with respect to the resolution necessary to characterize 10 micrometer faults. Analysis will also be more rapid with a lesser resolution. These adjustments depend of the device used and of the structures tested and are generally determined by tests.

Figure 4:
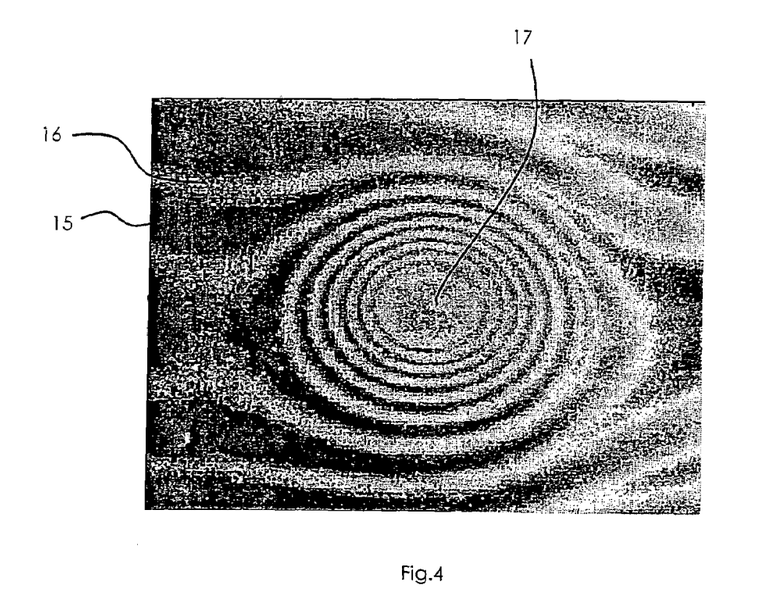
FIG. 4 shows an image that can be observed and recorded using an image acquisition means of a device according to the invention.

FIG. 4 shows an example of the image of the pattern of moiré fringes that image acquisition device 8 can record when passing over a surface damage. One observes on this figure dark fringes of low irradiance 15 and clear fringes of higher irradiance 16. These dark 15 and clear 16 fringes are no longer parallel; they are when there is no damage. On this figure, they form concentric patterns around the center of damage 17.

When the user of the device described here is faced with such observations, several options are open to him. He can either record or not the image of the pattern in the memory of image acquisition device 8 for each damage. He can also directly analyze the fault through the image acquisition device or on a screen that the image acquisition device might have. He can also pass across the whole structure to be analyzed and record all images at once and process them together afterwards with processing devices. He can also perform the process when each image is acquired.

The image is then analyzed by processing devices that will apply algorithms to obtain a representation of the damage observed on the basis of the pattern of the moiré fringes.

The standard mathematical model that gives the irradiance observed to a (x,y) position can be defined by:

$$I(x,y)=a(x,y)+b(x,y)\cos[\phi(x,y)],$$

where $a(x,y)$ and $b(x,y)$ represent respectively the background illumination and the amplitude, and $\phi(x,y)$ the phase containing the information that is of interest to us. In the case of the shadow moiré, $$\phi(x,y) = \frac{2\pi}{p}(\tan\alpha + \tan\beta)z$$

where p is the pitch of the grid, and $\alpha$ and $\beta$ are the lighting and observation angles, and z the height with respect to the reference plane.

In a first mode of implementation of the invention, one can consider the intensity of the fringes as locally monochromatic, as such the irradiance can be represented by a sinusoidal function modulated by a plane p(.). As such, by minimizing a cost function that takes into account the difference between the irradiance measured and the model proposed, one can obtain the $\phi(x,y)$ phase demodulation from irradiance I(x,y). In this particular mode of the invention, the cost function to be minimized for each point (x,y) is:

$$U(x,y) = \sum_{[\xi,\eta]\in(N_{x,y}\cap S)} \{[I'(\xi,\eta) - \cos p(x,y,\xi,\eta)]^2 + \beta[\phi_0(\xi,\eta) - p(x,y,\xi,\eta)]^2 m(\xi,\eta)\},$$

where $$p(x,y,\xi,\eta)=\omega_0(x,y)+\omega_x(x,y)(x-\xi)+\omega_y(x,y)(y-\eta),$$

where S is the region of interest where valid data are present; N(x,y) is the region adjacent to point (x,y) for which the phase is to be obtained; m(x,y) is an indicating field that is equal to 1 if the phase at point (x,y) has already been obtained, or 0 otherwise; $I^1(x,y)$ is a filtered and normalized high frequency version of irradiance I(x,y) that permits to eliminate beneficially the flow frequencies from background a(x,y) and to make the amplitude b(x,y)≈1. Fields $\omega_x(x,y)$ and $\omega_y(x,y)$ are estimates of local frequencies along axes x and y. These fields also represent the inclines of the phase plane. Finally, parameter $\beta$ is a constant that controls the regularity of phase $\phi_0(x,y)$.

To obtain phase demodulation, cost function U(x,y) must be minimized for each point on the basis of the variables $\phi_0(x,y)$, $\omega_x(x,y)$ and $\omega_y(x,y)$. However, this function is not linear. As such, quick optimization techniques cannot be used. A known method for resolving this problem consists of evaluating the phase and frequency components of $r(x,y)=(\phi_0, \omega_x, \omega_y)^T$ for each point starting from the recursion $$r^{x+1}=r^x-\mu\nabla_1 U(x,y),$$

where $\mu$ is the gradient descent step. Symbol ▼ is the gradient of U(x,y) on the basis of the three components of r.

This method requires an initial $r^0$ condition. When seed vector $r(x_o,y_o)$ is maximized, the regularity constant $\beta$ is not taken into account since the starting point is the first to undergo demodulation and consequently, the indicator function m(x,y) is equal to 0 for S. Once the seed vector $r(x_o, y_o)$ has been calculated, it is possible to continue with the rest of the points for S. This algorithm must follow a sequential and continuous path, point by point, starting with the seed point.

As indicated above, this algorithm sequentially demodulates the pattern drawn by the moiré fringes, by starting from a starting point and by extending subsequently until all of the area to be analyzed has been covered. The way of passing across the pattern is a critical phase of demodulation. When passing across the pattern of the moiré fringes, the purpose is to guide the algorithm so that the areas with the best quality are processed on a priority basis and the areas of lesser quality last. The effect of this technique is to limit possible errors only to the areas of lesser quality. To obtain a satisfactory quality map, for instance, the amplitude parameter b(x,y) can be used. In the case of phase offset, modulation of this parameter can be easily obtained. However, when using a single fringe pattern, such as in the invention, modulation is generally more difficult to achieve.

The technique used by the invention algorithm is to following the track of the pattern fringes, in other words, passing across the pattern along the isophase lines. This strategy has been described by Servin and Quiroga in their publication "Isochromatics demodulation from a single image using a regularized phase tracking technique" (M. Servin, J. A. Quiroga, Journal of Modern Optics, Volume 48, Number 3, 521-531, 2001). The principle consists of assigning a "quality" level for a grey level of the image. For instance, in an image with 256 levels of grey, one can arbitrarily select that the "best quality" areas correspond to those with grey levels of more than 128 and "low quality" areas to levels below 128. By using this principle, the image is divided in two zones or areas. Then, demodulation will take place on a priority basis for the "best quality" areas and then for the "low quality" areas, which means that the quality as defined through this technique, does not correspond to a high signal-noise ratio. From the irradiance of the fringe patterns, a two-level quality map can be built and one can demodulate on a priority basis the "best quality" areas to which, for instance, a value of 1 can be assigned and a 0 value to the "low quality" areas.

For a second mode of implementation of the invention, phase modulation is obtained in a different way. For this mode of implementation, the algorithm is looking for the quadratic signal of the fringes pattern. If the pattern can be described by $$I(x,y)=b(x,y)\cos[\phi(x,y)],$$

where $a(x,y) \approx 0$, the quadratic signal is given by $$Q_n\{I(x,y)\}=-b(x,y)\sin[\phi(x,y)],$$

where $Q_n\{\ \}$ is the quadratic operator. From this quadratic signal, one can determine the wrapped phase $W\{\phi(x,y)\}$ for the whole region to be analyzed by using the arctan function:

$$W\{\phi(x, y)\} = \arctan\left(\frac{-Q_n\{I(x, y)\}}{I(x, y)}\right),$$

where $W\{\ \}$ is the modulo $2\pi$ wrapping operator.

Knowing that in most of the practical situations, the $b(x,y)$ modulation is associated with a low frequency signal, an approximation of the $I(x,y)$ gradient can be obtained by $$\nabla I(x,y)=-b(x,y)\sin[\phi(x,y)]\nabla\phi(x,y).$$

By multiplying with $\nabla\phi(x,y)$, and by rearranging the terms, one obtains:

$$Q_n\{I(r)\} = \frac{\nabla \phi(r)}{|\nabla \phi(r)|} \frac{\nabla I(r)}{|\nabla \phi(r)|} = n_\xi(r)\frac{\nabla I(r)}{|\nabla \phi(r)|} = -b(r)\sin[\phi(r)]$$

According to this equation, one notices that the $Q_n\{\ \}$ quadratic operator is composed of two terms, a first $\mu_\phi$ orientation term, and a second that corresponds to a n-dimension isotropic generalization of the transform of the Hilbert space $$H_n\{I(x, y)\} = \frac{\nabla I}{|\nabla \phi|}.$$

This second term is a linear operator for which the Fourier transform corresponds to the nth filter of Reisz for a dimension along the spectral coordinates, in other words, $H_n\{,\}$ can be calculated by $$H_n\{I(r)\} = FT^{-1}\left\{i\frac{q}{|q|}FT\{I(r)\}\right\},$$

where $FT\{,\}$ corresponds to the Fourier operator and $q=(u,v)$ is the vector position in the spectral domain, which physically coincides with the spatial frequencies.

The first term $$n_\phi(r) = \frac{\nabla \phi(r)}{|\nabla \phi(r)|}$$

is a normal unit vector with corresponding isophasics, facing the direction of the orientation term of fringes $\nabla\phi(r)$. This terms linked to the direction of the fringes cannot be calculated directly because one can only access the phase through the irradiance and the orientation angles of the fringes calculated by the irradiance gradient do not correspond to the angles calculated by the phase gradient. As such, one has to unwrap the phase to obtain the orientation term of the fringes.

For unwrapping the orientation of the fringes, it is suggested to call upon an algorithm similar to the one described in the first mode of implementation above. Once the unwrapped fringe orientation map obtained, one can directly obtain the wrapped phase $W\{\phi(x,y)\}$ for the whole region to be analyzed. The last step of this mode of implementation as such consists of unwrapping the wrapped phase $W\{\phi(x,y)\}$.

For these two modes of implementation, modulation and variations of the background are undesirable because the cost function compares the values measured with the model of the fringe pattern: no background and a constant sinusoidal modulation. As such, in advance, the images of the fringe pattern must be processed to eliminate the background and to normalize the modulation.

The algorithm proposed here to achieve elimination of the background and normalization of the pattern is based on the quadratic operator described above.

As described above, the orientation field cannot be obtained directly from the phase gradient. On the other hand, a pseudo-orientation of the field can be calculated directly by the irradiance gradient $$\tilde{n}_\phi(r) = \frac{\nabla I}{|\nabla I|} = \text{sign}[\sin(\phi)]n_\phi(r)$$

According to this equation, $\tilde{n}_\phi$ and $n_{100}$ have the same orientation but opposite directions whenever $\sin(\phi)$ changes its sign. By using $\tilde{n}\phi$, rather than $n_{100}$, this change of sign leads to a new operator called quasi-quadratic operator:

$$\tilde{Q}_n\{I_{HP}\}=\tilde{n}(r)H_n\{I_{HP}\},$$

where $I_{HP}$ is the high frequency irradiance of the fringe pattern, in other words without the background, and for which it is assumed that it only includes low frequencies.

By substituting on the basis of the preceding equation, one obtains $$\tilde{Q}_n\{I_{HP}(r)\}=-\text{sign}[\sin\phi]m(r)\sin\phi(r).$$

Finally, one can calculate the phase modulation from this quasi-quadratic term $$W\{\tilde{\phi}\} = \arctan\left(\frac{-\tilde{Q}_n\{I_{HP}\}}{I_{HP}}\right) = \text{sign}[\sin\phi]W\{\phi\},$$

where $W\{,\}$ denotes the wrapping operator.

According to this equation, one sees how phase maps $W\{\tilde{\phi}\}$ and $W\{\phi\}$ only differ by their sign, whenever that $\sin(\phi)$ changes its sign. Consequently, one can calculate the normalized version of irradiance $I(r)$ from $W\{\tilde{\phi}\}$:

$$I_N(r)=\cos[W\{\tilde{\phi}(r)\}]=\cos\phi(r).$$

From a practical point of view, with respect to the invention, calculation of the $\tilde{n}_\phi$ orientation field is not necessary for normalization since the quasi-quadratic operator is defined by $$\tilde{Q}_n\{I\} = \frac{\nabla I}{|\nabla I|} \cdot \frac{\nabla I}{|\nabla\phi|} = \frac{|\nabla I|}{|\nabla\phi|},$$

as such, finally, the general expression used to calculate the quasi-quadratic operator is $$\tilde{Q}_n\{I_{HP}\}=|H_n\{I_{HP}\}|,$$

where, until now, $H_n\{\ \}$ is the n-dimensional Hilbert operator.

Using the first or the second mode of implementation depends on the system user. The second mode is quicker and is generally sufficient to represent the distortion for the pattern. The first mode on the other hand is more solid and is used when the results of the second mode are not very conclusive.

After having selected the algorithm to be used and the analysis of the pattern is performed, the user must specify for the system a image point for a zero height, which permits obtaining a complete representation of the distortion represented on the image by the fringe pattern.

For each point of the image, defined for instance by its position (x,y) on said image, the algorithms determine height z of the surface pertaining to such position.

Figure 5:
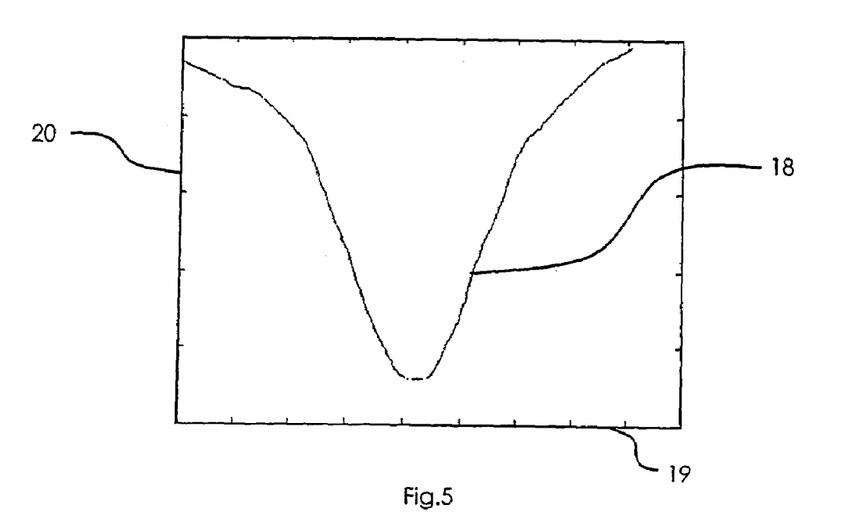
FIG. 5 is a two-dimensional representation of a damage on the basis of an image taken through the grid of FIG. 2.
Figure 6:
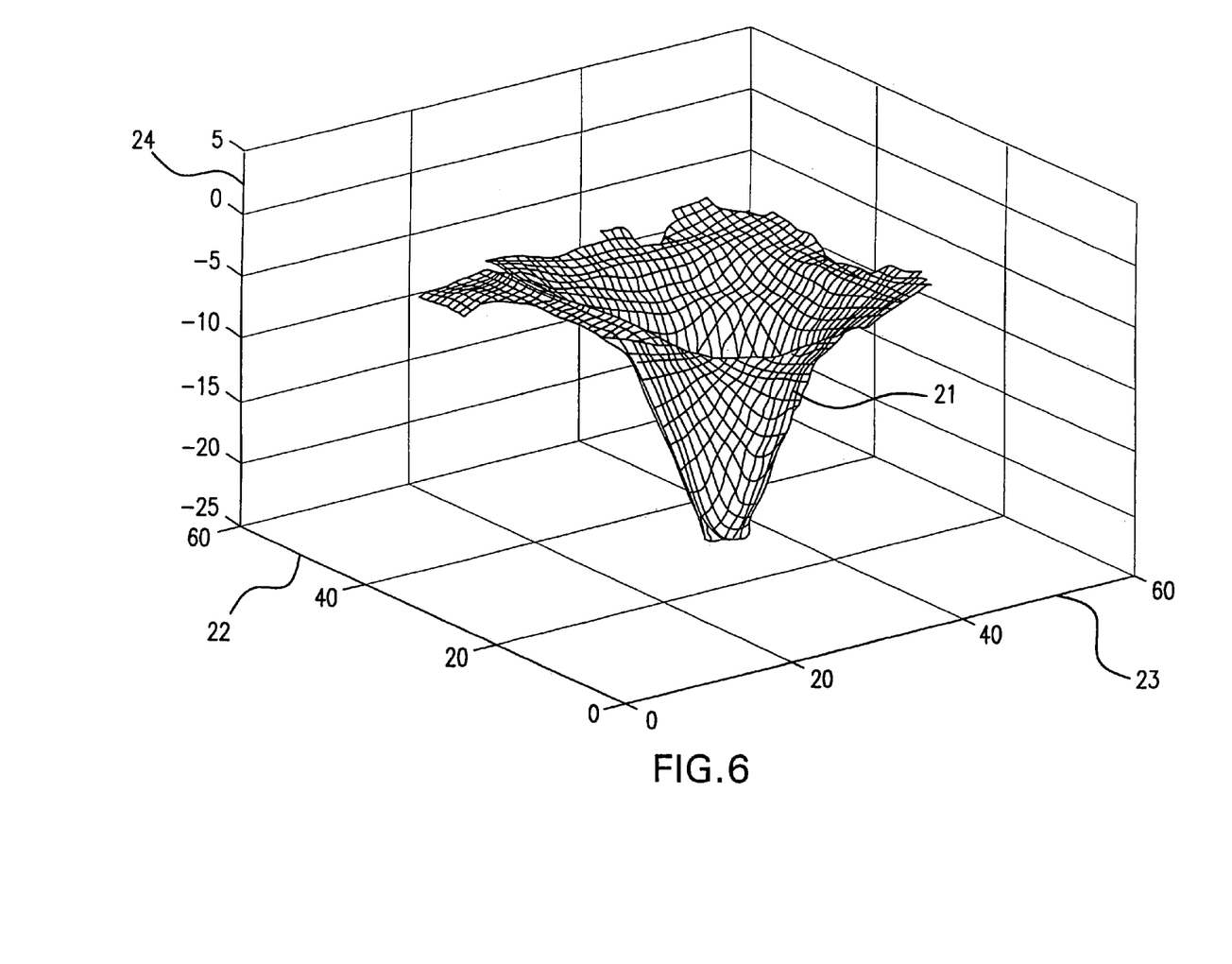
FIG. 6 is another representation, three-dimensional this time, of the damage on the basis of the image taken through the grid of FIG. 2.

FIGS. 5 and 6 present two of the different views that may be obtained by the algorithms described above.

FIG. 5 shows a two-dimensional view of a damage 18 obtained by the algorithms presented above. Scales 19, 20 with dimensions of about ten micrometers enable the user to characterize the damage shown on the basis of the various spatial positions of surface 18 in terms of width and depth, in a given direction. This type of two-dimensional view corresponds to a cross-section of the damage.

FIG. 6 illustrates a three-dimensional view of damage 21 obtained with the algorithms shown above. Scales 22, 23, 24 for which the unit is about ten micrometers, permit representing damage 21 accurately. To characterize the damage, various criteria can then be used. The characterization criteria depend on the application but starting with a complete geometry, the technical specialist can determine for instance whether certain predetermined maximum limits in one of the directions have been met.

The illustration of FIGS. 5 and 6 can also be a color illustration. A scale of colors can then be defined. For instance, it can be representative of the depth of the damage, the point where the deepest damage is located, may for instance be represented by a dark colors while the rest of the damage might be in a various color shades from height zero of the surface where the color would be lighter. Graphic illustration in color can be a view of two dimensions or of several dimensions of the damage.

This invention is not limited to the form of preferential implementation of the device described and illustrated on the drawings; nor is it limited to the variants of implementation of the process according to the invention presented above. This also involves all variants of implementation within reach of the technical specialist for the claims that follow.

What is claimed as new and desired to be secured by Letters Patent of the United States is:

1. A process for characterizing structural damage comprising:
    arranging a moir grid or screen near a surface of a structure;
    directing a light source towards said moir grid or screen so as to create a shadow of said moir grid or screen onto the structure;
    recording, using an acquisition device, an image of the pattern observed through the moir grid or screen according to a direction of observation different from that of the light source;
    graphically representing on a display the damage from said image recorded with a process algorithm of said image; and
    displaying on the display a depth of the damage based on said representation.

2. The process according to claim 1 further comprising:
    directly placing said moir grid or screen onto the surface to be analyzed.

3. The process according to claim 1 or 2, further comprising:
    running light from the light source across the surface;
    visually inspecting the existence or not of distortions of said pattern;
    stopping the passing of the light across the surface;
    recording an image using an acquisition device; and
    characterizing the damage.

4. The process according to claim 3, further comprising:
    transferring one or several recorded and unprocessed images to a storage device.

5. The process according to claim 4, wherein the process algorithm of the image comprises a normalized stage of interference fringes that appear on said image.

6. The process according to claim 4, wherein said algorithm performs phase modulation to determine a position in space of each point of said image, on the basis of mounting features and irradiance observed.

7. The process according to claim 1, wherein the result of the graphic representation stage of the damage is a graphic representation according to a color scale.

8. The process according to claim 1, wherein the result of said processing devices is transformed in a two-dimensional graphic representation of the damage.

9. The process according to claim 1, wherein the result of said processing devices is transformed in a graphic representation of several dimensions of the damage.

10. The process according to claim 1, further comprising:
repairing or replacing the structure based on the depth of the damage displayed in said displaying.

11. A device for characterizing a structural damage of a structural element comprising:
- a moir grid or screen over the structural element;
- a lighting device configured to emit light towards the moir grid or screen;
- an image acquisition device for which the observation axis is offset with respect to that of the lighting device, the image acquisition device configured to receive light reflected from the moir grid or screen to form an image;
- an image processing device configured to process the image to provide a graphical representation of the structural damage to the structural element including a depth of the structural damage; and
- a display device configured to display said graphical representation.

12. The device according to claim 11, wherein the moir grid or screen is flexible.

13. The device according to claim 11 or 12, wherein the moir grid or screen has undergone an anti-reflection treatment.

14. The device according to claim 11, wherein the image acquisition device is secured to the support.

15. The device according to claim 11, wherein a recording of the image is done by a digital acquisition device.

16. The device according to claim 15, wherein said record is processed by processing devices that apply image processing algorithms.

17. The device according to claim 11, further comprising:
- means for graphically transforming the result provided by the image processing device; and
- a screen for viewing the graphic representation obtained, permitting a representation according to a color scale, by two- or three-dimensional views.

* * * * *